United States Patent [19]

Mortazavi

[11] Patent Number: 5,411,532
[45] Date of Patent: May 2, 1995

[54] CARDIAC PACEMAKER HAVING INTEGRATED PACING LEAD AND OXYGEN SENSOR

[75] Inventor: Said Mortazavi, Granada Hills, Calif.

[73] Assignee: Pacesetter, Inc., Sylmar, Calif.

[21] Appl. No.: 73,225

[22] Filed: Jun. 4, 1993

[51] Int. Cl.⁶ .............................................. A61B 5/00
[52] U.S. Cl. ...................................... 607/22; 607/122
[58] Field of Search .................................. 607/22, 122

[56] References Cited

U.S. PATENT DOCUMENTS

| | | |
|---|---|---|
| 4,202,339 | 5/1980 | Wirtzfeld et al. . |
| 4,399,820 | 8/1983 | Wirtzfeld et al. . |
| 4,727,879 | 3/1988 | Liess et al. . |
| 4,750,495 | 6/1988 | Moore et al. . |
| 4,791,935 | 12/1988 | Baudino et al. . |
| 4,807,629 | 2/1989 | Baudino et al. . |
| 4,813,421 | 3/1989 | Baudino et al. . |
| 4,815,469 | 3/1989 | Cohen et al. . |
| 5,040,538 | 8/1991 | Mortazavi . |

*Primary Examiner*—William E. Kamm
*Assistant Examiner*—Scott M. Getzow
*Attorney, Agent, or Firm*—Malcolm J. Romano

[57] ABSTRACT

An improved cardiac pacemaker system of the kind that includes an oxygen sensor implantable into a patient's blood stream along with one or two electrical conductors for use in sensing heart beat activity and in selectively applying pacing pulses to the heart muscle. In an embodiment having just one implantable conductor, the oxygen sensor is integrated into the conductor, while in an embodiment having two implantable conductors, the oxygen sensor either is integrated into one of the conductors or is connected between the two conductors, in parallel with the heart muscle. In both cases, the oxygen sensor is selectively used without adversely affecting either heart beat sensing or pacing.

23 Claims, 4 Drawing Sheets

CARDIAC PACEMAKER HAVING INTEGRATED PACING LEAD AND OXYGEN SENSOR

BACKGROUND OF THE INVENTION

This invention relates generally to implantable cardiac pacemakers and, more particularly, to cardiac pacemakers having oxygen sensors of the kind that determine oxygen content by measuring the blood's reflectivity.

The cardiac pacemaker is perhaps one of the best known electronic marvels of modern medicine, and the implantation of a pacemaker in a patient has become almost a routine operation. The pacemaker pulses the patient's heart muscle continuously over an extended period of time, or in the case of demand pacemakers, monitors the heart muscle's natural operation and provides stimulating pulses only when the heart muscle skips a beat. Pacemakers allow patients with heart problems that otherwise would have been fatal or incapacitating to resume relatively normal lives.

The modern pacemaker is a highly complex device, capable of event sensing, two-way telemetry, and sensing and pacing in either or both of the atrium and the ventricle of the heart muscle. Such pacemakers may be finely tuned by the physician subsequent to implantation, and the parameters adjusted to provide optimum pacing performance.

Despite the sophistication of such pacemakers, a major difference remains between the healthy heart muscle and a paced heart muscle—namely, the response to activity or exercise. Variations in the cardiac stroke volume and systemic vascular resistance occur in the cardiovascular system due to physiological stresses such as exercise, temperature changes, postural changes, emotion, hypoglycemia, Valsalva maneuvers, etc.

To maintain adequate perfusion pressure and cardiac output under these stresses, it is necessary to adjust heart rate. The healthy heart muscle might beat at 60 or fewer beats per minute during repose or sleep, and at 120 or more beats per minute during strenuous exercise, for example. The heart muscle paced by a pacemaker that is non-rate responsive will typically beat at a constant rate of approximately 70 beats per minute.

It will be appreciated that the constantly-paced heart muscle will supply more blood than is needed during sleep, and might even prevent the patient from sleeping restfully. Even more seriously, patients paced at 70 beats per minute experience substantial difficulty in engaging in strenuous activity. Even a moderate level of activity such as walking will cause difficulty in some patients. It is apparent that a demand pacemaker whose rate varies in response to physiological need represents a highly desirable device that will enable patients requiring pacemakers to lead normal, active lives.

Physiologically-responsive cardiac pacing must optimize cardiac rate to the level of metabolic need in the absence of a normal variable cardiac rate. The simplest solution to this problem is atrial tracking pacing, where the patient has a full or partial AV block and a dual chamber pacemaker pulses the ventricle in response to normal cardiac activity sensed in the atrium. However, this technique is not possible in many patients with sinus bradycardia or atrial fibrillation, and so rate-responsive pacing is necessary to mimic the normal variable cardiac rate.

A variety of physiologically-responsive pacing systems have been proposed, which utilize a variety of physiological parameters as the basis for varying cardiac rate. These parameters include blood temperature, various sensed timing signals from the heart muscle, pressure measured within the heart muscle, respiratory rate, nervous system activity, physical activity, and blood chemistry.

Systems responsive to various blood chemistry parameters, such as blood oxygen saturation, are particularly worthwhile and effective. One such oxygen sensor is disclosed in U.S. Pat. No. 5,040,538, issued to Said Mortazavi and entitled "Pulsed Light Blood Oxygen Content Sensor System and Method of Using Same," which is incorporated herein by reference. The disclosed sensor includes an optical detector for measuring the mixed venous oxygen content, typically in the heart muscle's right ventricle. A diminution in the mixed venous oxygen content is used to produce a higher paced cardiac rate. The speed of this system is comparable to the time constant of the body, thereby enhancing its effectiveness.

The oxygen sensor disclosed in the prior patent includes a light-emitting diode or LED, positioned within the heart muscle's right ventricle and arranged such that any light it emits is directed at the blood within the ventricle, which reflects the light to an adjacent phototransistor. The amount of light so reflected is inversely related to the blood's oxygen content. The phototransistor is part of a circuit that is connected in parallel with the LED. When an electrical current pulse is supplied to the LED, the circuit begins integrating the resulting phototransistor current. When the integrated voltage reaches a predetermined threshold, the circuit latches and diverts the current pulse from the LED, to terminate its generation of light. The time delay from initiation of the measuring current pulse to latching of the circuit is inversely related to the blood's oxygen content level.

Two techniques for pacing the heart muscle are in common use. One technique, referred to as bipolar pacing, requires the implantation of two conductors. In this technique, the electrode end of one conductor is implanted in contact with the heart muscle while a second conductor is implanted with its electrode end in contact with blood in the heart muscle. Current pulses between these two conductors stimulate the heart muscle. A second technique, referred to as unipolar pacing, requires only a single conductor with its electrode end implanted in contact with the heart muscle. Instead of a second conductor, this technique uses the pacemaker's case, which is electrically connected to the pacemaker's circuitry, to provide an electrical connection to body tissue in the chest. This unipolar approach is subject to certain drawbacks. In this approach, the pacing pulse can stimulate not only the heart muscle, but also muscles in the chest that are located between the implantation site of the pacemaker and the heart muscle. Additionally, when the pacemaker needs to sense heart muscle activity, it also can sense activity of other muscles in the chest. Although not insurmountable, these are undesirable consequences.

Ideally from the standpoint of electrical simplicity, the interface to the oxygen sensor would consist of two conductors that are physically distinct from the two conductors used in bipolar pacing of the heart muscle. However, these four conductors would have to pass together as a single pacing lead through the vein, through the heart valve, and into the right ventricle of the heart muscle. As the number of conductors increases, the thickness and the stiffness of the pacing lead increases proportionally. This increases the difficulty of implanting the pacing lead into the heart muscle as well as the difficulty of the heart valve closing on the thicker pacing lead. Additionally, the pacing lead must connect to the pacemaker through a connector. As is well known in the art, the reliability of an electrical circuit generally will decrease with an increase in the number of connections. It is clearly imperative that a life-supporting device, such as a pacemaker, have as high a degree of reliability as possible. Thus, while it is highly desirable to add the feature of oxygen sensing to a pacemaker system, it would be even more advantageous if this feature could be added without increasing the number of conductors in the pacing lead.

In U.S. Pat. No. 5,040,538, this problem is addressed by committing an additional conductor to the oxygen sensor and by referencing the signals on this conductor to an electrical connection in common with the pacing signal. In a bipolar configuration, this results in a three-conductor implementation, while, in a unipolar configuration, this results in a two-conductor implementation. While accomplishing a goal of a two-conductor pacemaker with oxygen sensing, this implementation relies upon a unipolar approach with its previously-described drawbacks.

Thus, a need exists to provide the performance advantages of physiologically-responsive pacing by using an oxygen sensor but without increasing the number of conductors already required for bipolar or unipolar pacing. Thus, for a bipolar system an interconnection apparatus is needed that can additionally provide oxygen sensing with only two conductors, while for a unipolar system this requirement should be met with only a single conductor. The present invention satisfies these needs.

SUMMARY OF THE INVENTION

Briefly, and in general terms, the present invention resides in an implantable cardiac pacemaker system that incorporates oxygen sensing without requiring any additional conductors, thus simplifying implantation and improving reliability. This increased functionality without increasing the number of conductors is achieved by integrating the oxygen sensor into one of the conductors, or by connecting it between two conductors, and by arranging the oxygen sensor to receive and respond to current pulses having a polarity opposite that of pacing pulses selectively applied to the heart muscle.

More specifically, the pacemaker system of the invention comprises a pulse generator coupled to a patient's heart muscle through a first electrical conductor and an electrical return. The pulse generator intermittently generates pacing pulses of a first polarity through the first conductor and the electrical return. An oxygen sensor controller, connected in parallel with the pulse generator, intermittently generates sensing pulses of a second polarity, opposite of the first polarity, to control the oxygen sensor. The oxygen sensor and the pulse generator use a common set of conductors.

A diode distinguishes between the pacing and the oxygen sensing pulses, according to the direction of current flow. A heart sensing circuit is used to sense beats from the heart muscle. Again, this circuit uses the same conductors for its interface to the heart muscle. A resistor, in parallel with the current blocking device, permits the heart sensing circuit to sense both positive and negative voltages.

Other features and advantages of the present invention should become apparent from the following description of the preferred embodiments, taken in conjunction with the accompanying drawings, which illustrate, by way of example, the principles of the present invention.

DESCRIPTION OF THE PREFERRED EMBODIMENTS

Figure 1:
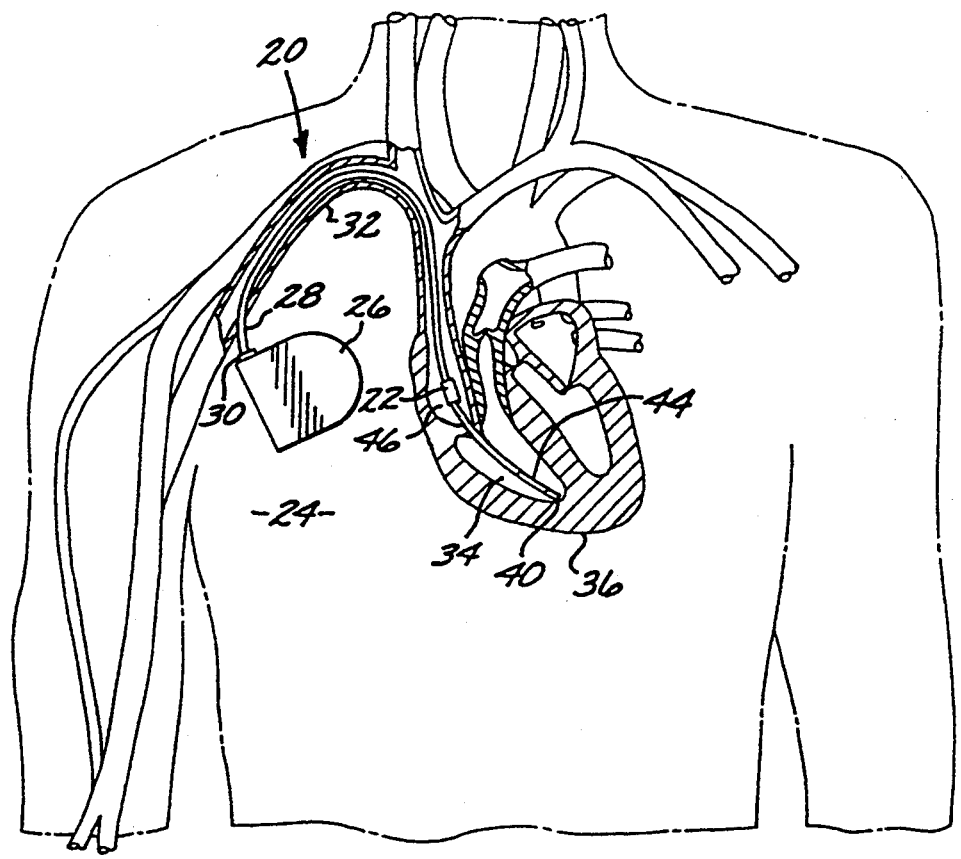
FIG. 1 is a diagrammatic illustration of the installation of the pacemaker system of the present invention in the chest cavity of a human being.

With reference now to the drawings, and particularly to FIG. 1, there is shown a bipolar pacemaker system 20 having an oxygen sensor 22 interconnected in accordance with the present invention, shown implanted in the right upper chest cavity of a patient 24. The pacemaker system includes a pacing unit 26 and a pacing lead 28, with a proximal end of the pacing lead connected through a connector 30 to the pacing unit and a distal end implanted through a vein 32 into the right ventricle 34 of the patient's heart muscle 36. Within the pacing lead are two electrical conductors, including a tip conductor 38 (not shown), to which is connected a tip electrode 40 at the pacing lead's distal end, and further including a ring conductor 42 (not shown), to which is connected a ring electrode 44 proximal to the pacing lead's distal end. The tip electrode is attached to the heart muscle, and the oxygen sensor 22 is integrated into the pacing lead in the right atrium 46 of the heart muscle. The ring electrode is located between the tip electrode and the oxygen sensor, in contact with the blood flowing through the heart muscle, and it forms an electrical return for signals from the tip electrode. In FIG. 1, the oxygen sensor 22 is located in the heart muscle's right atrium 46, although it will be appreciated that the oxygen sensor alternatively could be located in the vein 32 leading to the heart muscle or in the heart muscle's right ventricle 34.

Flexibility of the pacing lead 28 is an important factor in a successful and efficient threading of the pacing lead through the vein 32 and into the heart muscle 36. The tip electrode 40 is located in the right ventricle 34, and thus the pacing lead must extend through a valve 48 located between the right ventricle and the right atrium 46. Since the valve must successfully close around the pacing lead and prevent the back flow of blood, the pacing lead should be as thin as possible. Additionally, the possibility of failure will generally increase with the number of separate conductors present in the pacing lead or in the connector 30. Thus, a goal and accomplishment of the present invention is to minimize the number of conductors within the pacing lead and in the connector. Thus, a goal and accomplishment of the present invention is to minimize the number of conductors within the pacing lead and in the connector.

In the bipolar pacemaker system of FIG. 1, pacing pulses are provided to the heart muscle 36 by applying voltage pulses of approximately −2 volts to the tip electrode 40 relative to the ring electrode 44. This typically induces a current pulse of about 4 milliamps. It will be appreciated that, because blood is conductive and because the tip electrode contacts the heart muscle 36 and the ring electrode contacts the blood within the heart muscle, this current path is completed within the heart muscle without involving other body tissues in the patient's chest.

Figure 2:
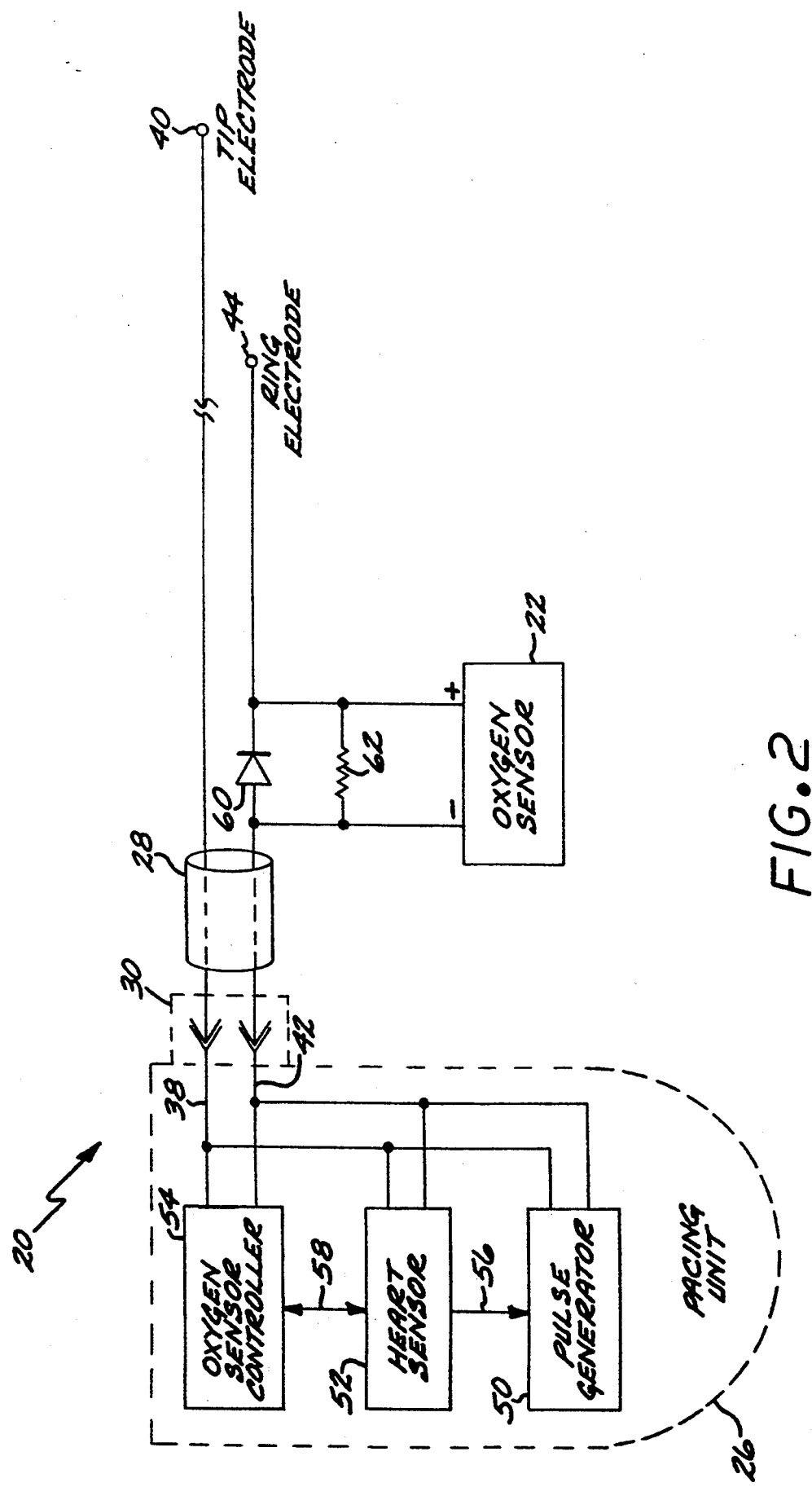
FIG. 2 is a simplified block diagram of a first embodiment of a pacemaker system in accordance with the present invention, including a two-conductor pacing lead and an oxygen sensor integrated into one of the two conductors.

With reference now to FIG. 2, there is shown a block diagram of the pacemaker system 20, of FIG. 1. The pacing unit 26 is shown to include three main circuits, including a pulse generator 50, a heart sensor 52, and an oxygen sensor controller 54. The pulse generator 50 intermittently generates pacing pulses of approximately −2 volts on the tip conductor 38 relative to the ring conductor 42, when it is determined that the heart muscle 36 has failed to produce a timely beat. The heart sensor 52 determines such a failure to produce a timely beat by monitoring the voltage across the same tip and ring conductors to detect a characteristic voltage pattern. When the heart sensor determines that a failure to produce a timely beat has occurred, it transmits a pulse demand signal on line 56 to the pulse generator 50, which then generates a pacing pulse.

The oxygen sensor controller 54 periodically transmits sense pulses via the conductors 38 and 42 to the oxygen sensor 22, to measure the blood's oxygen content. If the oxygen sensor controller determines that the oxygen level is below a predetermined threshold, it transmits a sense demand signal on line 58 to the heart sensor 52, which responds by increasing the rate at which it anticipates its detection of heart beats. It therefore will generate pulse demand signals for coupling on line 56 to the pulse generator after a reduced time period of failing to detect a heart beat.

In the pacemaker system 20 of FIG. 2, the oxygen sensor 22 is integrated into the ring conductor 42, proximal to the ring electrode 44, and it is connected in parallel with a diode 60 and a resistor 62. The diode is oriented to conduct current in a direction toward the ring electrode, which corresponds to the direction that current flows during a pacing pulse. A Schottky diode is preferably used, to minimize the voltage drop and the corresponding power loss across the diode during pacing.

Sensing pulses generated by the oxygen sensor controller 54 are of polarity opposite to that of the pacing pulses. Current is therefore induced to flow from the tip electrode 40 through the heart muscle 36 to the ring electrode 44. Because the diode 60 is reverse biased, the current is caused to pass through the oxygen sensor 22. Operation of the oxygen sensor is discussed below, with reference to FIG. 3.

Although the current induced by the sensing pulses flows through the heart muscle 36, undesired additional heart beats are not induced, for two reasons. First, the current flow required by the oxygen sensor 22 is only about 400 microamps, as contrasted with the 4 milliamps typically required for stimulating the heart muscle. Second, the heart muscle is not susceptible to being immediately re-stimulated since oxygen sensing pulses are transmitted during a time period directly following either a normal or stimulated heart beat.

The resistor 62 is used for sensing the characteristic positive and negative voltage pattern that is generated by the heart muscle 36 each time it beats. Without the resistor, the diode 60 would restrict the heart sensor 52 from reading both voltage polarities across the tip conductor 38 and the ring conductor 42. The resistor's resistance can be sufficiently large to not adversely affect the current-blocking function of the parallel-connected diode 60. The resistor also provides a conduction path for a recharge current that follows any pacing pulse. The desired recharge rate must be considered when selecting the resistance value. A resistance value of 20 kilohms is considered suitable.

The pacing units 26 therefore operates in four modes using the tip conductor 38 and ring conductor 42. These modes are heart sensing, pacing, recharge, and oxygen sensing, all of which are repeated periodically during different time periods. First, heart sensing occurs to determine if there is a need for a pacing pulse. During heart sensing, the heart sensor 52 uses the resistor 62 to read both positive and negative voltages from the heart muscle 36. Second, if a heart beat is not sensed within a predetermined time period, the pulse generator 50 will be triggered to transmit a negative voltage pacing pulse on the tip conductor relative to the ring conductor. The resulting current is conducted through the diode 60 to the heart muscle. Third, a recharge time period follows the transmission of each pacing pulse, during which current is allowed to flow through the heart muscle in a reverse direction from the pacing pulse. This recharge current flows through the resistor 62, which is connected in parallel with the diode. Fourth, during oxygen sensing, the oxygen sensor controller 50 transmits a positive voltage pulse on the tip conductor relative to the ring conductor. Based upon the above description, it should be noted that the recharge and oxygen sensing could be combined to reduce overall power consumption.

Figure 3:
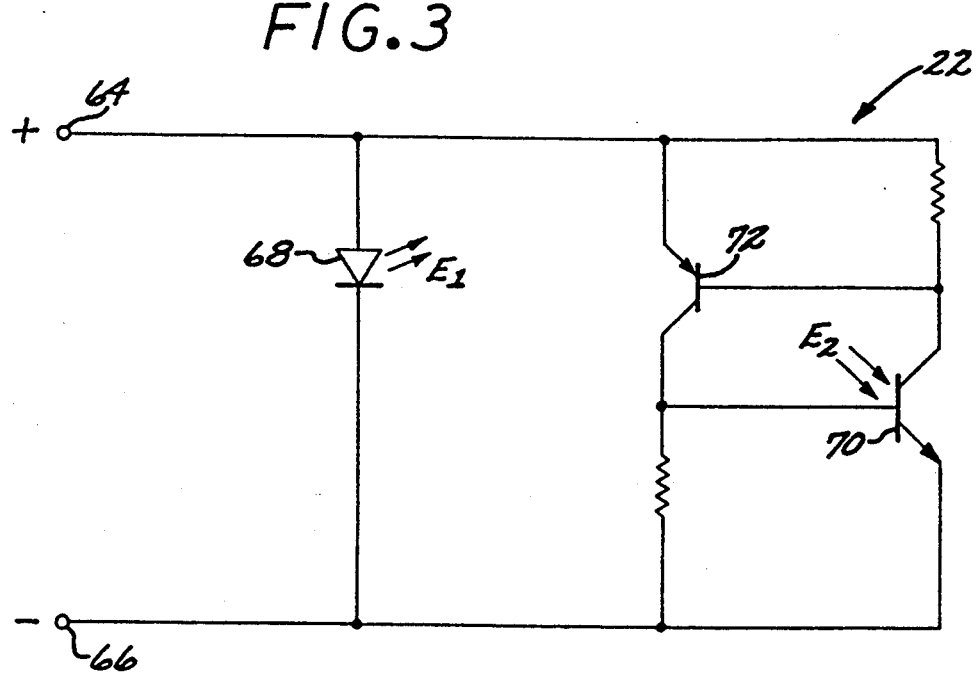
FIG. 3 is a schematic circuit diagram of the oxygen sensor of the pacemaker system of FIG. 2.

With reference now to FIG. 3, there is shown a schematic diagram of the oxygen sensor 22. This oxygen sensor is disclosed in detail in U.S. Pat. No. 5,040,538, which is incorporated by reference. Briefly, the oxygen sensor includes a light-emitting diode (LED) 64 connected between a positive input terminal 66 and a negative input terminal 68. When a positive voltage is applied across the terminals, the LED is caused to emit light $E_1$ that is directed at the adjacent blood. Reflected light $E_2$ is then produced in an intensity indicative of the blood's oxygen content. An phototransistor 70 is positioned to receive this reflected light $E_2$ and, with its associated circuitry, integrates a voltage proportional to the light's intensity. When this integrated voltage reaches a prescribed value, a threshold detector 72 is biased ON, to shunt current from the LED. The resulting change in voltage is sensed by the sensor controller 54 (FIG. 2) using the same conductors 38 and 42 that supply the current to the oxygen sensor. The time delay from initiation of the sensing pulse until the threshold detector 72 is biased ON constitutes a measure of the blood's oxygen content.

With reference again to FIG. 2, the integration of the oxygen sensor 22 into the ring conductor 42 is further discussed. As previously mentioned, the oxygen sensor, the diode 60, and the resistor 62 are all connected in parallel with each other. When the pacing unit 26 transmits a pacing pulse along the conductors 38 and 42, current is induced to flow from the ring electrode 44 to the tip electrode 40, in which case the current is conducted forwardly through the diode 60. No current flows through the oxygen sensor, because its LED 64, phototransistor 70, and threshold detector 72 are all reverse biased.

On the other hand, when the pacing unit 26 transmits an oxygen sensing pulse along the conductors 38 and 42, current is induced to flow from the tip electrode 40 to the ring electrode 44, in which case the current is conducted through the oxygen sensor 22. No current flows through the diode 60, because it is reverse biased.

While the resistor 62 is required for heart beat sensing and recharge, this resistor complicates the interface requirements to the oxygen sensor 22. As taught in U.S. Pat. No. 5,113,862, which is incorporated by reference, any resistance in parallel with the oxygen sensor can cause the threshold detector 72 to prematurely shunt the LED 68. The patent also teaches that this situation can be remedied by first ramping a small initialization current to a level just below that required for illuminating the LED and by then increasing the supplied current to a value above this threshold, to illuminate the LED. This leakage compensation is performed by monitoring the voltage level across the LED, i.e., the voltage between the tip conductor 38 and ring conductor 42. The measured voltage is attributable to the desired LED voltage plus the voltage drop between the tip electrode 40 and the ring electrode 44. The resistance of the heart muscle 36, which interconnects the tip and ring electrodes, is approximately 500 ohms. Since the 20 kilohm resistor 62 is connected in series with the heart muscle, approximately 500/(20,000+500) or 1/41 of the measured voltage will be present across the tip and ring electrodes. Consequently, approximately 40/41 of the measured voltage will be present across the LED. This minor correction can be accommodated by the leakage compensation circuit described in U.S. Pat. No. 5,113,862.

The pacemaker system 20 depicted in FIG. 2 integrates the oxygen sensor 22, diode 60 and resistor 62 into the ring conductor 42. In a modified embodiment (not shown in the drawings), these components are integrated into the tip conductor 38. In this modified embodiment, the oxygen sensor and diode, of course, are oriented in a direction opposite that depicted in FIG. 2.

Figure 4:
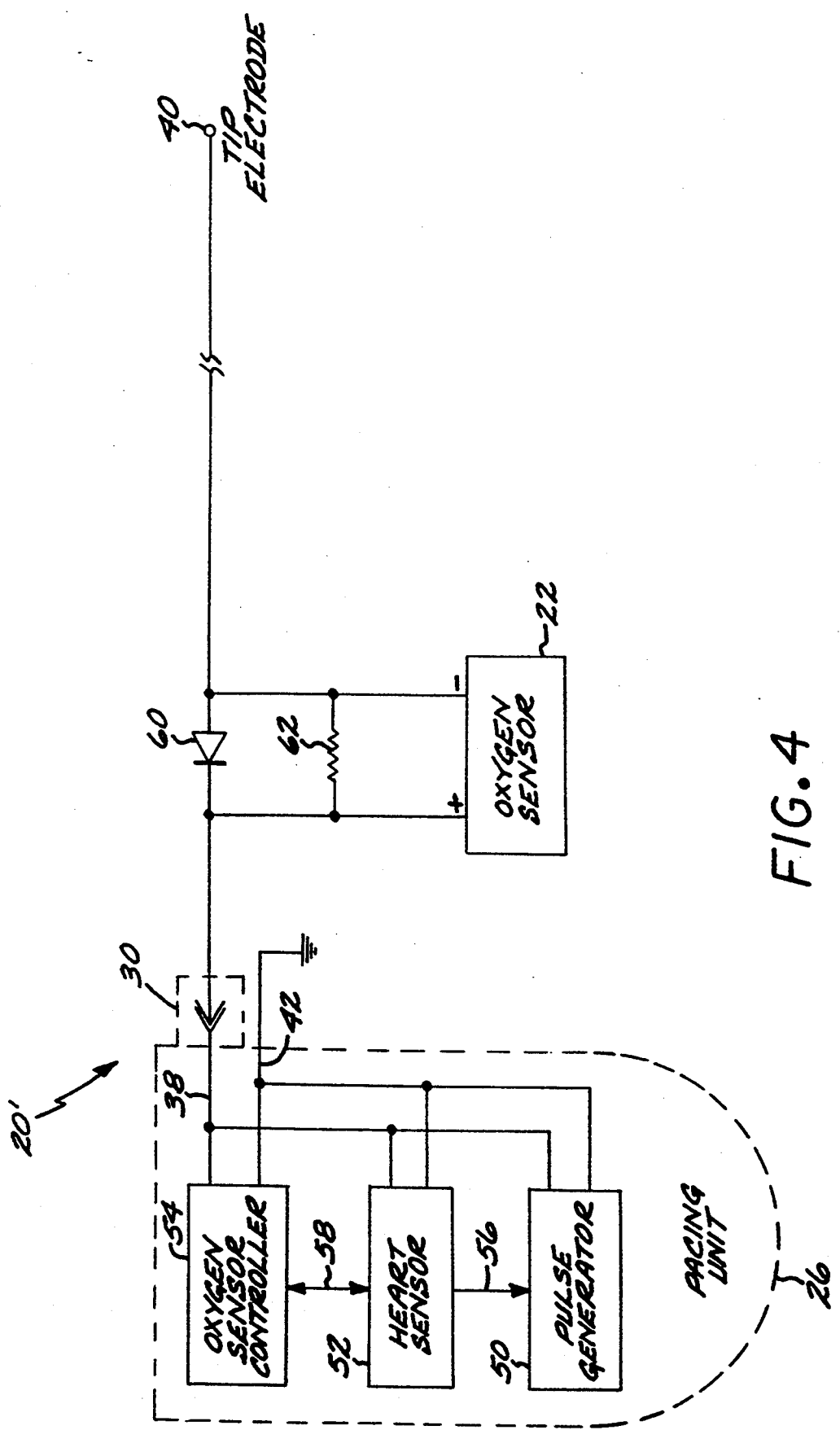
FIG. 4 is a simplified block diagram of a second embodiment of a pacemaker system in accordance with the present invention, including a one-conductor pacing lead and an oxygen sensor integrated into that conductor.

With reference now to FIG. 4, there is shown another embodiment of a pacemaker system 20' in accordance with the invention. This embodiment differs from the FIG. 2 embodiment in that it includes the tip conductor 38 and tip electrode 40, but eliminates the ring conductor 42 and ring electrode 44. It thus is referred to as a unipolar implementation, with the conductive case of the pacing unit 26 functioning as the second electrode. The oxygen sensor 22, diode 60 and resistor 62 are integrated into the tip conductor.

The pacemaker system 20' of FIG. 4 functions similarly to the pacemaker system 20 of FIG. 2, except that current flowing during pacing and sensing must pass between the tip electrode 40 and the case of the pacing unit 26, which contacts body tissue in the patient's chest. This current path includes intervening body tissues; outside of the heart muscle 36, such that additional, undesirable muscular stimulation can occur. Also, the pacing unit 26 can unavoidably sense muscular activity outside of the heart muscle when it periodically senses voltages across the same current path. These complications make a unipolar implementation less desirable.

Figure 5:
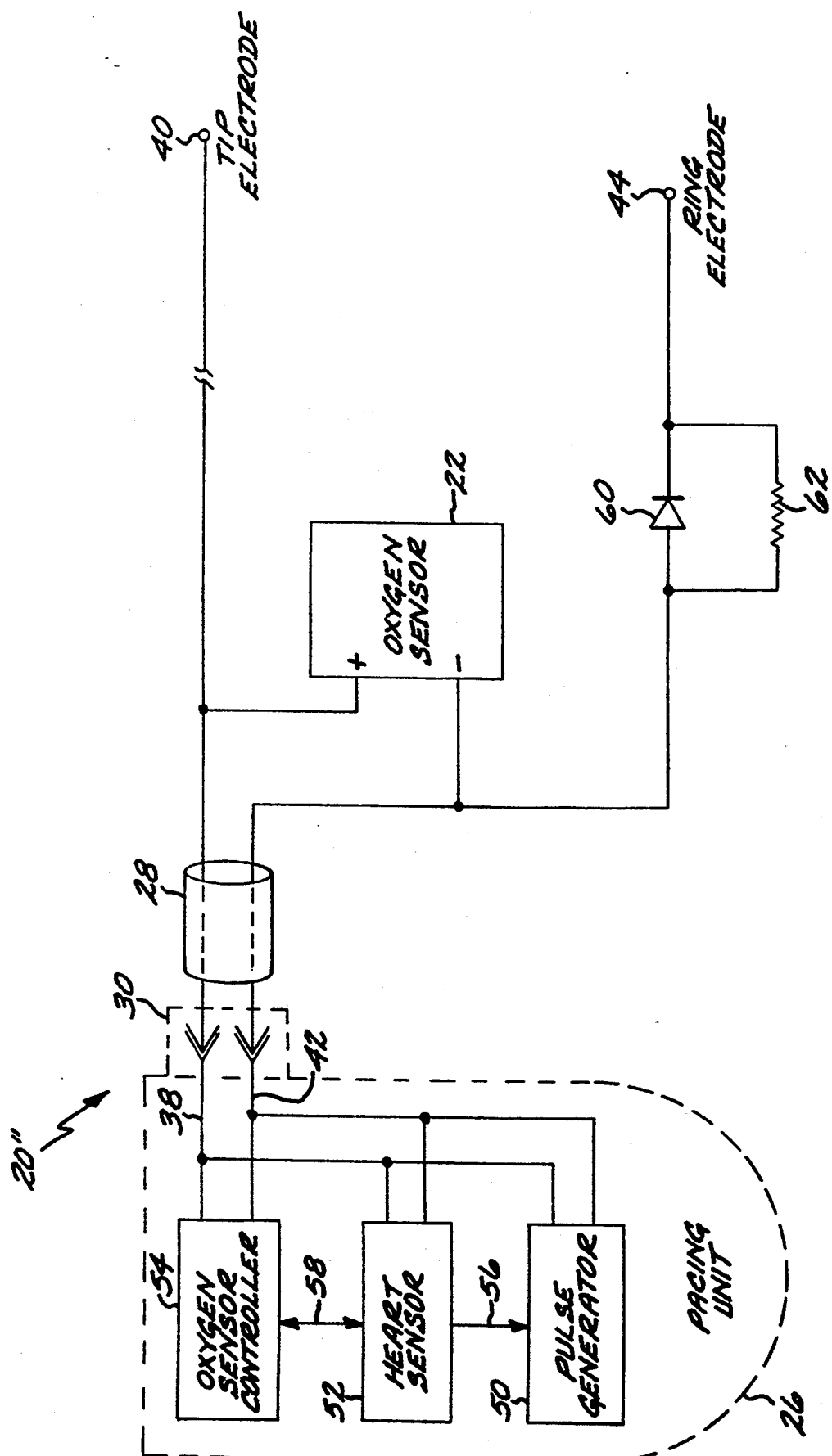
FIG. 5 is a simplified block diagram of a third embodiment of a pacemaker system in accordance with the present invention, including a two-conductor pacing lead and an oxygen sensor connected between the two conductors.

With reference now to FIG. 5, there is shown a block diagram of yet another embodiment of a pacemaker system 20' in accordance with the invention. Like the FIG. 2 embodiment, the FIG. 5 embodiment connects the pacing unit 26 to the heart muscle 36 and to the oxygen sensor 22 via the tip conductor 38 and the ring conductor 42. Further, the diode 60 and the resistor 62 are connected in parallel and integrated into the ring conductor 42. In contrast with the FIG. 2 embodiment, however, the FIG. 5 embodiment connects the oxygen sensor between the tip conductor and the ring conductor. The FIG. 5 embodiment thus is referred to as a parallel implementation.

In a manner similar to the previously-described embodiments, a negative voltage pacing pulse present on the tip conductor 38 relative to the ring conductor 42, during the pacing mode, induces a current to flow through the diode 60 to stimulate the heart muscle 36. No current flows through the oxygen sensor 22 at this time because its components are reverse biased.

During the heart sensing and recharge modes, the diode 62 again blocks one polarity of the current. Thus, as in the prior embodiments, the resistor 62 30 provides a bidirectional path, independent of polarity, to perform the functions called for in these modes. Complications arising from the location of the oxygen sensor 22 are discussed below.

During the oxygen sensing mode, a positive voltage is applied to the tip conductor 38 relative to the ring conductor 42. The diode 60 therefore is reverse biased at this time and only minimal current is directed, via the resistor 62, through the heart muscle 36. The oxygen sensor 22 is connected directly across the tip and ring conductors, so it operates substantially independently of the diode 60 and the resistor 62.

It will be noted that the oxygen sensor 22 of the FIG. 5 embodiment is effectively connected in parallel with a series combination of the resistor 62 and the heart muscle 36. As previously mentioned, the resistor preferably has a resistance of about 20 kilohms, and the heart muscle typically provides a resistance of about 500 ohms. This parallel resistance can lead to a premature triggering of the oxygen sensor and, therefore, can lead to an inaccurate determination of oxygen concentration. U.S. Pat. No. 5,113,862, referred to above, discloses one suitable technique for compensating for this parallel resistance.

During the recharge mode, the pacing unit 24 delivers current to the heart muscle 36 via the diode 60 and resistor 62. In supplying the recharge current, an account must be made for the presence of the oxygen sensor 22, which shunts the heart muscle. In particular, the pacing unit must account for the oxygen sensor's operating mode, i.e., whether or not the threshold detector 72 of the oxygen sensor is conducting current.

In a modification of the pacemaker system embodiment 20' of FIG. 5 (not shown in the drawings), the diode 60 and resistor 62 can be integrated into the tip conductor 38 instead of the ring conductor 42. It will, of course, be appreciated that the polarity of the diode will need to be reversed in such a modified embodiment.

It should be appreciated from the foregoing description that the present invention provides an improved implantable pacemaker system that incorporates an oxygen sensor without requiring any additional implanted conductors. This is achieved by integrating the oxygen sensor into on the conductors used for pacing the heart and by utilizing the oxygen sensor only during time periods when pacing pulses are not being applied to the heart.

Although the present invention has been described in detail with reference only to the presently-preferred embodiments, those of ordinary skill in the art will appreciate that various modifications can be made without departing from the invention. Accordingly, the invention is defined by the following claims.

What is claimed is:

1. An implantable cardiac pacemaker system including a pulse generator for generating pacing pulses, the system further including:
   at least one electrical conductor having a proximal end for electrically interfacing with the pulse generator and a distal end for electrical contact with selected heart muscle,
   said pulse generator further selectively coupling pacing pulses along the at least one conductor to electrically stimulate the patient's heart muscle;
   an oxygen sensor circuit connected in series circuit arrangement with the at least one conductor;
   means for generating oxygen sensing pulses; and
   an oxygen sensor circuit controller for intermittently coupling oxygen sensing pulses to the oxygen sensor circuit along the at least one conductor for measuring the oxygen content of the patient's blood.

2. A cardiac pacemaker system, as defined in claim 1, wherein:
   the pacing pulses are of a first polarity; and
   the oxygen sensing pulses are of a second polarity, opposite to the first polarity.

3. A cardiac pacemaker system, as defined in claim 2, wherein the oxygen sensor circuit includes a diode connected in series circuit arrangement with the at least one conductor and adapted to conduct current of the first polarity and to block current of the second polarity.

4. A cardiac pacemaker system, as defined in claim 3, and further comprising:
   a heart sensor connected in parallel with the pulse generator; and
   a resistor connected in parallel with the diode.

5. A cardiac pacemaker system, as defined in claim 4, wherein the oxygen sensor circuit includes an oxygen sensor and the diode is connected in parallel with the oxygen sensor.

6. An implantable cardiac pacemaker system comprising:
   a first electrical conductor implantable in contact with a patient's heart muscle;
   a second electrical conductor implantable in contact within the patient's bloodstream, the first and second electrical conductors having electrical voltages thereon as a function of heartbeats;
   an oxygen sensor circuit connected to either or both of the first and second electrical conductors and implantable within the patient's blood; and
   a pacing pulse generator for generating pacing pulses, the pulse generator including
   a heart sensor for monitoring the relative voltages present on the first and second electrical conductors, to detect the occurrence of a heart beat, said pulse generator further selectively coupling pacing pulses along the first and second electrical conductors, to electrically stimulate the heart muscle;
   an oxygen sensor controller for generating oxygen sensing pulses and for intermittently coupling oxygen sensing pulses along the first and second electrical conductors to the oxygen sensor circuit, to measure the oxygen content of the patient's blood, said pacing pulses being of a first polarity; and
   the oxygen sensing pulses being of a second polarity, opposite the first polarity; and wherein the oxygen sensor circuit further comprises:
   a diode integrated into either the first conductor or the second conductor, for conducting current of the first polarity and blocking current of the second polarity; and
   a resistor connected in parallel with the diode.

7. An implantable cardiac pacemaker system as defined in claim 6, wherein the oxygen sensor circuit further comprises an oxygen sensor connected in parallel with the diode and the resistor.

8. An implantable cardiac pacemaker as defined in claim 6, wherein the oxygen sensor circuit is connected between the first electrical conductor and the second electrical conductor.

9. A body implantable sensor and lead comprising:
   an implantable stimulating lead having a connector at one end thereof for interfacing with a desired pacing pulse generator;
   an electrode at the other end thereof for contacting selected heart muscle, the stimulating lead including:
   an electrical conductor coupled between the connector and the electrode for conducting pacing pulses from the desired pacing pulse generator to the selected heart muscle;
   sensor means electrically inserted in series with the conductor for sensing a specific characteristic of body fluid proximal the sensor means, the sensor means responsive to a drive signal for generating an output signal that varies as a function of the specific body fluid characteristic; and
   controller means for intermittently transmitting the drive signal and the pacing pulses along the conductor.

10. The body implantable sensor and lead of claim 9, wherein the controller means further comprises means for monitoring the sensor means output signal along the conductor.

11. The body implantable sensor and lead of claim 10, wherein the drive signal is of a first polarity and the pacing pulse is of a second polarity opposite to the first polarity.

12. The body implantable sensor and lead of claim 11, wherein the sensor means comprises a blood oxygen sensor, the body fluid is blood, and the specific characteristic is blood oxygen.

13. The body implantable sensor and lead of claim 12, wherein the sensor means includes a diode coupled to the conductor for conducting current of the first polarity, and for blocking current of the second polarity.

14. The body implantable sensor and lead of claim 13, wherein the oxygen sensor includes means for emitting a measuring signal in the blood in response to the drive signal and means for receiving a portion of said measuring signal reflected back to said oxygen sensor by the blood, the portion of the measuring signal reflected back to said oxygen sensor being proportional to the oxygen content of the blood.

15. A pacemaker lead adapted for transmitting pacing pulses for unipolar pacing, the lead having a single electrical conductor and an oxygen sensor circuit electrically inserted in series with said single electrical conductor, such that pacing pulses transmitted through the single electrical conductor are transmitted through the oxygen sensor circuit.

16. The pacemaker lead of claim 15, wherein the oxygen sensor circuit includes a diode electrically inserted in series with said conductor for conducting current of a first polarity and blocking current of a second polarity which is opposite to the first polarity.

17. The pacemaker lead of claim 16, wherein the oxygen sensor circuit includes a resistor connected in parallel with the diode.

18. The pacemaker lead of claim 17, wherein the oxygen sensor circuit further comprises a blood oxygen sensor connected in parallel with the diode and the resistor.

19. A pacemaker lead adapted for transmitting pacing pulses for bipolar pacing, the lead having two electrical conductors and an oxygen sensor circuit electrically inserted in series with one of said two electrical conductors, such that pacing pulses transmitted through such one of said two electrical conductors are transmitted through the oxygen sensor circuit.

20. The pacemaker lead of claim 19, wherein the oxygen sensor circuit includes a diode electrically inserted in series with said conductor for conducting current of a first polarity and blocking current of a second polarity which is opposite to the first polarity.

21. The pacemaker lead of claim 20, wherein the oxygen sensor circuit includes a resistor connected in parallel with the diode.

22. A pacemaker lead for delivering pacing pulses from a desired pacing pulse generator to a desired location in the heart, comprising:
 first and second electrical conductors;
 means for electrically interfacing the first and second electrical conductors with the pulse generator;
 a ring electrode;
 a tip electrode, one of said first and second conductors coupled from the interfacing means to one of said ring and tip electrodes, the other one of said first and second conductors coupled from the interfacing means to the other one of said ring and tip electrodes; and
 a blood oxygen sensor circuit inserted in series circuit arrangement with either one of said first and second conductors, such that pacing pulses pass through the blood oxygen sensor circuit.

23. A pacemaker lead for delivering pacing pulses from a desired pacing pulse generator to a desired location in the heart, the lead comprising:
 first and second electrical conductors;
 means for electrically interfacing the first and second electrical conductors with the pulse generator;
 a ring electrode;
 a tip electrode, one of said first and second conductors coupled from the interfacing means to one of said ring and tip electrodes, the other one of said first and second electrodes coupled from the interfacing means to the other one of said ring and tip electrodes;
 a diode inserted in series circuit arrangement with either one of said first and second conductors;
 a resistor in parallel circuit arrangement with the diode; and
 a blood oxygen sensor electrically coupled to and in parallel circuit arrangement with the first and second conductors.

* * * * *